(12) United States Patent
Royds

(10) Patent No.: US 7,776,266 B2
(45) Date of Patent: Aug. 17, 2010

(54) CONSUMER FOOD TESTING DEVICE

(75) Inventor: Robert B. Royds, Plainsboro, NJ (US)

(73) Assignee: Harrogate Holdings, Hamilton (BM)

( * ) Notice: Subject to any disclaimer, the term of this patent is extended or adjusted under 35 U.S.C. 154(b) by 22 days.

(21) Appl. No.: 12/321,287

(22) Filed: Jan. 20, 2009

(65) Prior Publication Data

US 2009/0136633 A1    May 28, 2009

Related U.S. Application Data

(62) Division of application No. 11/401,726, filed on Apr. 11, 2006, now Pat. No. 7,527,765.

(51) Int. Cl.
C12Q 1/68 (2006.01)
B01L 3/00 (2006.01)
G01N 33/53 (2006.01)

(52) U.S. Cl. .......................... 422/68.1; 422/50; 422/55; 422/56; 422/57; 422/58; 422/61; 422/70; 422/71; 422/101; 435/4; 435/286.1; 435/287.1; 435/288.7; 436/164; 436/175; 436/177; 436/518

(58) Field of Classification Search ........................ None
See application file for complete search history.

(56) References Cited

U.S. PATENT DOCUMENTS

| | | | |
|---|---|---|---|
| 4,020,046 A | 4/1977 | King et al. | 260/900 |
| 4,822,174 A | 4/1989 | Deibel | 366/279 |
| 4,933,092 A | 6/1990 | Aunet et al. | 210/729 |
| 5,075,078 A | 12/1991 | Osikowicz et al. | 422/56 |
| 5,096,837 A | 3/1992 | Fan et al. | 436/514 |
| 5,218,208 A | 6/1993 | Augier et al. | 250/363.02 |
| 5,229,073 A | 7/1993 | Luo et al. | 422/56 |
| 5,275,785 A | 1/1994 | May et al. | 422/56 |
| 5,354,692 A | 10/1994 | Yang et al. | 436/514 |
| 5,452,716 A | 9/1995 | Clift | 128/633 |
| 5,504,013 A | 4/1996 | Senior | 436/165 |
| 5,602,040 A | 2/1997 | May et al. | 436/514 |
| 5,622,871 A | 4/1997 | May et al. | 436/514 |
| 5,656,503 A | 8/1997 | May et al. | 436/514 |
| 5,695,946 A | 12/1997 | Benjamin et al. | 435/7.32 |
| 6,046,057 A | 4/2000 | Nazareth et al. | 436/514 |
| 6,180,335 B1 | 1/2001 | Wilkins et al. | 435/4 |
| 6,268,209 B1 | 7/2001 | Pierson et al. | 435/287.9 |
| 6,277,650 B1 | 8/2001 | Nazareth et al. | 436/514 |
| 6,441,142 B1 | 8/2002 | Burks et al. | 530/387.9 |
| 6,565,808 B2 | 5/2003 | Hudak et al. | 422/58 |
| 6,616,893 B1 | 9/2003 | Pham | 422/58 |
| 6,828,110 B2 | 12/2004 | Lee et al. | 435/7.1 |
| 7,098,040 B2 | 8/2006 | Kaylor et al. | 436/514 |
| 2004/0018575 A1 | 1/2004 | Rappin et al. | 435/7.92 |
| 2004/0132091 A1 | 7/2004 | Ramsey et al. | 435/7.1 |
| 2004/0132211 A1 | 7/2004 | Li | 436/514 |
| 2004/0259226 A1 | 12/2004 | Robey et al. | 435/252.3 |
| 2005/0106652 A1 | 5/2005 | Massey et al. | 435/15 |
| 2007/0047382 A1 | 3/2007 | McCurdy et al. | 366/153.1 |
| 2007/0054414 A1 | 3/2007 | Burgess-Cassier et al. | 436/514 |

FOREIGN PATENT DOCUMENTS

WO    WO 2005/006959 A2    1/2005

OTHER PUBLICATIONS

"Securing the Home Planet, Technologies developed by NASA's Office of Biological and Physical Research To Keep Air, Water, and Food Safe For Astronauts in Space Can Also Help Protect People On Earth From Bioterrorism"; http://exploration.nasa.gov/articles/homeplanet_lite.html; Oct. 14, 2005; National Aeronautics and Space Administration, pp. 1 through 12.

S. De Saeger and C. Van Peteghem; "Dipstick Enzyme Immunoassay To Detect Fusarium T-2 Toxin In Wheat"; AEM; copyright 1996 by the American Society of Microbiology; http://aem.asm.org/cgi/content/abstract/62/6/1880; Oct. 13, 2005; p. 1.

Laurian Unnevehr, Tanya Roberts, and Carl Custer; "New Pathogen Testing Technologies and the Market for Food Safety Information; "AgBio Forum, The Journal of Agrobiotechnology Management & Economics; vol. 7, No. 4, Article 7; http://www.agbioforum.org/v7n4/v7n4a07-unnevehr.htm; Oct. 13, 2005; pp. 1 through 12.

(Continued)

Primary Examiner—Lisa V Cook
(74) Attorney, Agent, or Firm—Watov & Kipnes, P.C.; Kenneth Watov

(57) ABSTRACT

A food testing device for testing for the presence of harmful contaminants in a food sample, includes a vessel adapted for holding a liquefied food sample, a liquefier operatively associated with the vessel for converting an unliquefied food sample into a liquefied food sample, at least one test assay dispensable from the device, wherein the test assay includes at least one assay reagent having an affinity for at least one harmful contaminant, and capable of both detecting the presence of the harmful contaminant in the liquefied food sample, and producing a visual cue upon recognition of the harmful contaminant; and a radiation detector disposed proximately to the vessel for indicating the presence of ionizing radiation in the food sample at amounts exceeding normal background levels to detect the presence of a radioactive agent as the harmful contaminant.

2 Claims, 2 Drawing Sheets

OTHER PUBLICATIONS

"Hepatitis C Test" "Ampac Hepatitis C (HCV) Dipstick Assay"; Ampac Asia; http://www.ampacasiapacific.com/hepC.html; Oct. 13, 2005; pp. 1through4.

Huey-Fen Shyu et al.; "Hybridoma and Hybridomics Monoclonal Antibody-Based Enzyme Immunoassay for Detection of Ricin"; Feb. 2002, vol. 21, No. 1: 69-73; http:www.liebertonline.com/doi/abs/10.1089/15368590252917665; Mary Ann Liebert Inc. Publishers; Oct. 13, 2005; p. 1 of 1.

Clare Aldus, Gary Wyatt, Mike Peck of Institute of Food Research (IFR) and Aart van Amerongen Renata Ariëns, Jan Wichers of Agrotechnological Research Institute (ATO); "Multi-Analyte Detection of Verotoxin-Producing *E. coli* in Foods; Development of Rapid, Solid-Phase, Dipstick Method for Cells and Toxin"; UK Food Standards Agency.

Ira Shah and C.T. Deshmukh; A Bedside Dipstick Method to Detect *Plasmodium falciparum*; Indian Pediatrics 2004; 41:1148-1151; http://www.indianpediatrics.net/nov2004/nov-1148-1151.htm; Oct. 13, 2005; pp. 1-5.

C.F. Aldus, et al.; "Principles of Some Novel Rapid Disptick Methods for Detection and Characterization of Verotoxigenic *Escherichia coli*"; Journal of Applied Microbiology, vol. 95, No. 2, Aug. 2003, pp. 380-389(10); ingentaconnect; http://www.ingentaconnect.com/content/bsc/jam/2003/00000095/00000002/art00023; Oct. 13, 2005; pp. 1-1.

Gholam-Hossein Edrissian et al.; "Rapid Immunochromatography Test 'ICT Malaria Pf' in Diagnosis of *Plasmodium falciparum* and its Application in the in vivo Drug Susceptibility Test"; School of Public Health and Institute of Public Health Research, Tehran University of Medical Sciences, Tehran, Iran; http://www.ams.ac.ir/AIM/0141/edrissian0141.html; Oct. 13, 2005, pp. 1-4.

BioTerror Test; Standard Diagnostics, Inc. http://www.standardia.com/eng_product/bio_terror.asp; Oct. 14, 2005; pp. 1-2.

N. Rahmah et al., "Specificity and Sensitivity Of A Rapid Dipstick Test (Brugia Rapid) in the Detecton of Brugia Malayi Infection"; Science Direct; Transactions of the Royal Society of Tropical Medicine and Hygiene; vol. 95, Issue 6;, Nov.-Dec. 2001; pp. 601-604; http://www.sciencedirect.com/science?_ob=ArticleURL&_udi=B75GP-4BY324P-YR&_coverD; Oct. 13, 2005; pp. 1-2.

Se-Hwan Paek et al.; "Development of Rapid One-Step Immunochromatographic Assay"; Science Direct; Methods, vol. 22, Issue 1; Sep. 2000; pp. 53-60; http://www.sciencedirect.com/science?_ob=ArticleURL&_udi=B6WN5-45S48T1-CC&_coverD; Oct. 13, 2005; pp. 1-2.

"Scintillation Counter"; http://www.education.yahoo.com/reference/encylcopedia/entry/scintill; Oct. 13, 2005; pp. 1-2.

"Scintillation Counter"; http://en.wikipedia.org/wiki/Scintillation_counters; Oct. 13, 2005; p. 1.

Helena Enroth et al., "Diagnostic Accuracy of a Rapid Whole-Blood Test for Detection of *Helicobacter pylori*"; Journal of Clincial Microbiology, vol. 35, No. 10; Oct. 1997; pp. 2695-2697.

Andreas Hackelsberger et al.; " Performance of a Rapid Whole Blood Test for *Helicobacter pylori* in Primary Care: A German Multicenter Study"; Helicobacter, vol. 3, No. 3; 1998; pp. 179-183.

Wai Keung Leung et al.; "Comparison of Two Rapid Whole-Blood Tests for *Helicobacter pylori* Infection in Chinese Patients"; Journal of Clinical Microbiology, vol. 36, No. 11; Nov. 1998; pp. 3441-3442.

P. Andersen, et al.; "Specific Immune-based Diagnosis of Tuberculosis"; Review, The Lancet, vol. 356; Sep. 23, 2000; pp. 1099-1104.

"Ricin Toxin Detection Kit -For smooth Surface and solution detection"; BioWarfare Agent Detection Devices; Osborn Scientific Group; Feb. 27, 2003; pp. 1-2.

Renee Dilulio; "A Whole New World"; medical devicelink, IVDT archive originally in IVD Technology; http://www.devicelink.com/ivdt/archive/02/05/003.html; May 2002; pp. 1-7.

Beacon Melamine Plate Kit; Cat. #MTP-031; 5 pages—http://www.sceti.co.jp/medical.

CONSUMER FOOD TESTING DEVICE

The present Application is a Divisional of prior application Ser. No. 11/401,726, filed on Apr. 11, 2006 now U.S. Pat. No. 7,527,765, and claims priority therefrom.

FIELD OF THE INVENTION

The present invention relates to safety testing of foodstuffs, and more particularly to a portable testing device for use by consumers to detect the presence of harmful contaminants in foodstuff to avoid consumption of contaminated food.

BACKGROUND OF THE INVENTION

Recent events in the world have given rise to concerns about unconventional terrorist attacks using biological, chemical, and/or radioactive weapons of mass destruction. These events have further heightened international awareness of the vulnerability of food and water supplies of nations to terrorist attacks. Certain biological, chemical and/or radioactive agents can be used in such attacks to dangerously contaminate food and water supplies. Such contamination may have widespread destructive effects on a large population resulting in large numbers of fatalities, serious acute long-term health effects such as fetal abnormalities, paralysis, blindness, physical disfigurement, and mental debilitation, and chronic illnesses such as cancer. The deliberate contamination of food and water is a real and current threat.

The U.S. Centers For Disease Control and Prevention (CDC) has identified several harmful contaminants that can be critical agents for possible terrorist attacks. Among the high-priority biological agents ("Category A" agents) are *Bacillus anthraces* (anthrax) and *Clostridium botulinum* (botulism), both of which are deadly pathogens and can be used to contaminate food and water.

The majority of harmful contaminants identified by CDC were classified as "Category B" agents because they are moderately easy to disseminate and cause moderate morbidity and low mortality. Some of the Category B agents include *Salmonella* spp. such as *Salmonella typhimurium* and *Salmonella enteritidis, Shigella* spp. such as *Shigella dysenteriae, Escherichia* spp. such as *E. coli* 0157:H7 and *E. coli* non-O157:H7 STEC, *Campylobacter* spp. such as *Campylobacter jejuni, Listeria* spp. such as *Listeria monocytogenes*, and the like.

The CDC further identified certain chemicals as possible agents for terrorist attack. Those include pesticides, dioxins, furans, polychlorinated biphenyl (PCBs), cyanides, heavy metals such as arsenic, lead and mercury, and other natural and synthetic persistent toxins including mycotoxin and marine toxin. The CDC has warned that terrorists may use various combinations of these agents, and/or implement attacks in more than one location simultaneously.

These agents are also known to pose significant threat in the event that they are inadvertently introduced into the food and water distribution chain due to unintentional contamination of food (e.g., through processing failures or handling errors) unrelated to terrorism. Major outbreaks of food poisoning occur all too frequently, sometimes affecting hundreds of thousands of people.

Some examples of large-scale outbreaks caused by unintentional contamination include, among other incidences, an outbreak of *Salmonella enteritidis* infection linked to a contaminated ice cream pre-mix sickened an estimated 224,000 people in 41 states in the U.S. in 1984, an outbreak of *Salmonella typhimurium* infection linked to post-pasteurization contamination of milk from a U.S. dairy plant sickened approximately 170,000 people in 1985; an outbreak of hepatitis A, which may be the largest food borne disease incident in history, caused by tainted clams affected nearly 300,000 people in China in 1991; and an outbreak of *Escherichia coli* 0157:H7 linked to tainted radish sprouts served in school lunches sickened about 8,000 children with some dead in Japan in 1996.

The World Health Organization (WHO) has estimated that about two million children worldwide die from food and water contaminated by pathogenic microbes every year. In developed countries, one out of every three has suffered from some form of a food poisoning every year. It is estimated that about 76 million illnesses, 325,000 hospitalizations, and 5,000 deaths occur annually due to food/water contamination in the U.S.

Food poisoning from contamination with pesticides, natural and synthetic toxins, marine toxins, mycotoxins, heavy metals, cyanide, and other acutely toxic chemicals also have been reported. In one deadly incident in 1981, a cooking oil product sold in Spain contaminated with a chemical agent that killed over 800 people and injured about 20,000. In 1985, nearly 1,400 people in the U.S. reported becoming ill after eating watermelon grown in soil treated with the pesticide aldicarb. During 1971-72, more than 6,500 people were hospitalized with neurological symptoms and 459 died after eating bread made from mercury-contaminated wheat in Iraq. Additionally, in the 1960's, more than 200 people in Japan suffered from mercury poisoning after eating highly contaminated fish caught in polluted waters.

In today's global marketplace, the contamination of food in one country can have a significant effect on public health in other parts of the world. In 1989, approximately 25,000 people in 30 states in the U.S. were sickened by *Salmonella chester* in cantaloupes imported from Mexico. In 1996 and 1997, 2,500 people in 21 states in the U.S. and two Canadian provinces developed *Cyclospora* infections after eating tainted Guatemalan raspberries.

Accordingly, there is a need for a food testing device designed to implement rapid real-time testing of foodstuffs prior to consumption. There is a further need for a food testing device that is compact, portable and simple to use with little or no training in laboratory techniques. There is a further need for a food testing device that is designed to prevent or minimize the incidence of illness, injury and death caused by deliberate or unintentional contamination of food and water.

SUMMARY OF THE INVENTION

The present invention relates generally to a consumer food testing device useful for implementing rapid, real-time testing of foodstuffs prior to consumption. The food testing device of the present invention is compact and portable, and intended for use by a consumer at any location including their home or in a restaurant, for example. The food testing device of the present invention is designed to analyze and detect in food potentially harmful contaminants including chemical agents, biological agents and radioactive agents, and alert the user prior to consumption. The food testing device can further be adapted to detect food specific allergens that may cause the consumer to exhibit effects of hypersensitivity or allergic reaction.

The food testing device of the present invention is capable of analyzing small amounts of food samples, and can be implemented by consumers without extensive training in laboratory techniques. The food testing device is simple and cost effective to construct and implement, its compact size greatly enhances portability and discreet operation, while effectively acting to prevent a user from consuming contaminated food.

The food testing device of the present invention is designed to process a food sample into a form that can be tested by test assays. The test assays utilized are preferably in the form of a dipstick assay including chromatographic assays such as flow through and lateral flow assays, or other dipstick assays. Most preferably, the test assay is a lateral flow assay in the form of a dipstick. The use of lateral flow assays yields a relatively simple one-step analysis process that can easily be implemented by inexperienced users.

In general, a lateral flow assay typically includes an elongated rectangular component, often of paper, nitrocellulose or other porous inert material, upon which are printed stripes or layers of assay reagents having particular affinity for a target substance (i.e., harmful contaminant). The lateral flow assay includes a sample end, which is dipped into a sample, and the fluid is drawn along the strip by capillary action. As the sample passes the zones of assay reagents, chemical reactions occur which may result in a visual cue or color change, which can be in the form of one or more stripes, for example.

In one aspect of the present invention, there is provided a food testing device for testing for the presence of harmful contaminants in a food sample, which comprises:

a vessel adapted for holding a liquefied food sample; and at least one test assay dispensable from the device, the test assay comprising at least one assay reagent having an affinity for at least one harmful contaminant, and capable of both detecting the presence of the harmful contaminant in the liquefied food sample, and producing a visual cue upon recognition of the harmful contaminant.

In a further aspect of the present invention, there is provided a food testing device for testing for the presence of harmful contaminants in a food sample, which comprises:

a vessel adapted for holding a liquefied food sample;

a liquefier operatively associated with said vessel for converting an unliquefied food sample into a liquefied food sample; and at least one test assay dispensable from the device, the test assay comprising at least one assay reagent having an affinity for at least one harmful contaminant, and capable of both detecting the presence of the harmful contaminant in the liquefied food sample, and producing a visual cue upon recognition of the harmful contaminant.

Preferably, the food testing device further comprises a radiation detector disposed proximately to the vessel for indicating the presence of ionizing radiation in the food sample at amounts exceeding normal background levels to detect the presence of a radioactive agent as the harmful contaminant.

In another aspect of the present invention, there is provided a method for testing for the presence of a harmful contaminant in a food sample, comprising the steps of:

liquefying the food sample to yield a liquefied food sample; and implementing at least one test assay comprising an assay reagent having an affinity for at least one harmful contaminant and capable of both detecting and visually indicating the presence of the harmful contaminant in the liquefied food sample.

BRIEF DESCRIPTION OF THE DRAWINGS

The following drawings, in which like items may have the same reference designations, are illustrative of embodiments of the present invention and are not intended to limit the invention as encompassed by the claims forming part of the application, wherein:

DETAILED DESCRIPTION OF THE INVENTION

The present invention relates generally to a consumer food testing device useful for implementing rapid, real-time testing of foodstuffs prior to consumption, for preventing consumption of contaminated food. The food testing device of the present invention is intended for use by a consumer at any location including their home or in a restaurant. The food testing device of the present invention is designed to analyze and detect potentially harmful contaminants including chemical agents, biological agents and/or radioactive agents, and alert the user prior to consumption. The food testing device can be adapted to detect specific food allergens that may cause the consumer to exhibit effects of hypersensitivity or allergic reaction. The food testing device of the present invention is designed to analyze small amounts of food samples, and can be implemented by consumers without extensive training in laboratory techniques.

The food testing device of the present invention ensures that the food is safe for human consumption in a rapid, real-time manner, and is substantially free of harmful contaminants that can be dangerous to the consumer. The present invention operates to prevent or substantially minimize the incidence of food contamination due to improper handling or sabotage, while reducing the complexity of the testing process and the time needed to implement such tests. The food testing device is simple and cost effective to construct and implement, and its compact size greatly enhances portability and discreet operation.

In one embodiment of the present invention, there is provided a food testing device for testing the presence of harmful contaminants in a food sample, which comprises a vessel adapted for holding a liquefied food sample; and at least one test assay dispensable from the device. The at least one test assay comprises at least one assay reagent having an affinity for at least one harmful contaminant, and capable of both detecting the presence of the harmful contaminant in the liquefied food sample, and producing a visual cue upon recognition of the harmful contaminant.

In preferred embodiment of the present invention, the food testing device can further include a liquefier operatively associated with said vessel for converting an unliquefied food sample into a liquified food sample.

In a more preferred embodiment of the present invention, the food testing device can further include a radiation detector disposed proximately to the vessel for indicating the presence of ionizing radiation in the food sample at amounts exceeding normal background levels to detect the presence of a radioactive agent as the harmful contaminant.

Figure 1:
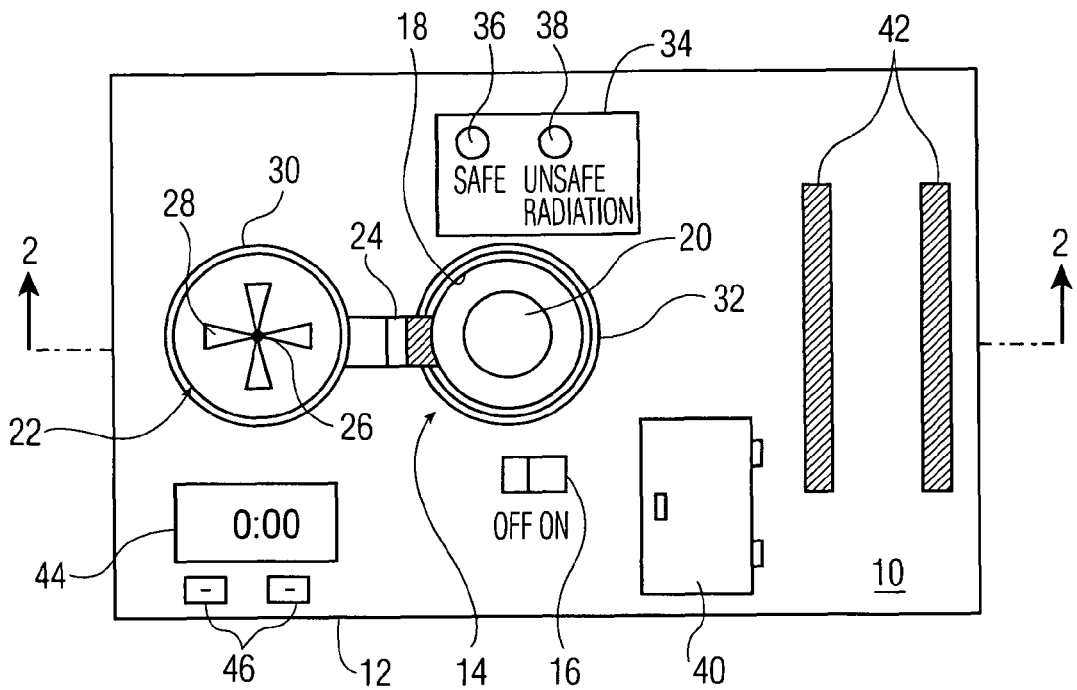
FIG. 1 is a top plan view of a food testing device for one embodiment of the present invention.

Referring to FIG. 1, a food testing device is shown and identified generally by reference numeral 10. The food testing device 10 is preferably constructed to be small and compact for portability and discreet use, and is used to process and test small sample amounts of food and/or drinks for the presence of potentially harmful contaminants to provide enhanced consumption safety and prevent illnesses, injury and possibly death due to food poisoning.

Representative examples of potentially harmful contaminants include any of those selected from persistent toxic substances that can remain viable for long periods of time in food and water, and can readily be spread through food and drink products to the end consumer. Such persistent toxic substances can be chemical agents (e.g., heavy metals, pesticides, toxins, chemical substances), biological agents (e.g., pathogens, disease infections) or radioactive agents or combinations thereof, and/or specific allergens that may trigger adverse reactions in certain sizable portions of the population.

The food testing device 10 comprises a base or substrate 12 supporting a liquefier assembly 14 for converting food into a liquid or puree form. The liquefier assembly 14 includes a power switch 16 for electrical connection to a power source (not shown) such as a rechargeable battery, a vessel 18 for receiving and holding a disposable sample container 20, and a blade assembly 22 connected through a hinge 24 to the vessel 18. The container 30 is adapted to receive and retain a small sample amount of food and/or liquid. The food testing device 10 can further include an optional container dispenser (not shown) located in the base 12 for dispensing a fresh disposable sample container 20 for each testing use.

The blade assembly 22 includes a blade housing 30 and a centrally-located spindle 26 extending from the blade housing 30 with a plurality of mixing blades 28 disposed therearound. The mixing blades 28 are configured to cut and break up any solids that may be present in the food sample and convert it into a puree form. The mixing blades 28 can be detached from the spindle 26 for cleaning. A motor (not shown) contained in the blade housing 30 mechanically drives the spindle 26 and the plurality of blades 28 during operation.

The food testing device includes a radiation detector assembly 32 disposed around the vessel 18. The radiation detector assembly 32 is designed to detect and measure the presence of any ionizing radiation emanating from the food and/or liquid sample at amounts exceeding normal background radiation levels. The radiation detector assembly 32 informs the consumer of the amount of the ionizing radiation emanating from the food sample.

This information is conveyed through an indicator assembly 34 comprising a "safe" indicator light 36 and an "unsafe" indicator light 38. Alternatively, the indicator assembly can be a measurement gauge. If the level of the ionizing radiation is detected above a predetermined threshold for safety, the unsafe indicator 38 is activated to warn the consumer to avoid the respective food due to elevated levels of radioactivity, and possible contaminating presence of a radioactive agent. For example, generally caesium and strontium are found in milk, in which the safe levels of radioactivity should be below 1 kBq/Kg (one Kilobecquerel/Kilogram). Note that all other isotopes should have a radioactivity below 1 KBq/kg.

The radiation detection assembly 32 can be selected from any suitable ionization radiation detection devices including a Geiger counter, a scintillation counter, a photo multiplier, an ionization chamber, a semiconductor detector, a radiation dosimeter, and combinations thereof.

In an alternative embodiment, the radiation detection assembly can be in the form of a radioactive test assay utilizing chemical reagents to indicate the presence of a radioactive agent through reaction with the ionizing radiation emanating from the food sample. The radioactive test assay can be held proximate the food sample to detect dangerous ionizing radiation, in which the assay changes color or produces a visual cue as a visual indication of dangerous radioactivity contaminating the food sample.

The food testing device 10 further includes a test supply compartment 40 for accommodating and storing test assays (not shown) preferably in the form of dipstick assays including chromatographic assays such as flow through assays and lateral flow assays. Such test assays have been adapted for detecting specific components in a food sample through a simple one step process. A storage area 42 provides for holding the test assays during testing of the food sample as will be described hereinafter. The test assays are configured to receive a portion of the food sample from the liquefier assembly 14 after processing, to test the food sample for contaminants. A timer 44 with control buttons 46 allows the consumer to determine and monitor the completion of the test assays to check results.

The test assays are preferably in the form of a dipstick assay including chromatographic assays such as flow through assays or lateral flow assays, or other dipstick assays. Most preferably, the test assay is a lateral flow assay. Such test assays are known in the art, and can readily be constructed and designed by those skilled in the art to detect specific contaminants. They are also commercially available from various suppliers including, for example, the Food Safety segment of Neogen Corporation of Lansing, Mich. As discussed above the use of lateral flow assays yields a relatively simple one-step analysis process that can be implemented by inexperienced users. Suitable examples of commercial products include the REVEAL™ line of test assays marketed by Neogen Corp. for detecting *E. coli* O157:H7, *Listeria* spp., *Salmonella* spp., *Salmonella enteritidis*, peanut allergen, aflatoxin, deoxynivalenol and other dangerous substances in food and animal feed.

Generally, a lateral flow assay typically includes an elongated stick or rectangular component, often of paper, nitrocellulose or other porous inert material, upon which are printed stripes or layers of assay reagents having particular affinity for a target substance (i.e., harmful contaminant). The lateral flow assay includes a sample end, which is dipped into a sample, and the fluid is drawn along the strip by capillary action. As the sample passes the zones of assay reagents, chemical reactions occur which may result in visual cues or color changes, which can be in the form of one or more stripes, for example, to indicate the presence of one or more target substances or contaminants, in this example. Such lateral flow assays and assay reagents are known in the art.

A variety of reagents can be used to detect a range of analytes to alert the user of the presence of harmful contaminants and food allergens in foodstuffs, and can be derived from immunodiagnostic, enzymatic, lateral flow immunochromatography or chemistry type reactions. The reagent used in the test assays of the present invention can be any substance having a specific affinity for a target substance or analyte corresponding to food allergens or toxic substances, including chemical agents and biological agents that may be present in food stuffs and represent a dangerous threat to the health of the consumer.

Suitable reagents can be selected from those that can provide detection for harmful contaminants such as biological agents including, but not limited to, pathogens such as *Escherichia* spp. (e.g., *E. coli* O157:H7), *Bacillus* spp. (e.g., *Bacillus anthracis* and *Bacillus cereus*), *Clostridium* spp. (e.g., *Clostridium botulinum* and *Clostridium perfringens*), *Campylobacter* spp. (e.g., *Campylobacter jejuni*), *Salmonella* spp. (*Salmonella enteritidis* and *Salmonella typhi*), *Listeria monocytogenes*, *Shigella* spp., *Streptococcus* spp., *Vibrio* spp. (e.g., *Vibrio cholerae, Vibrio parahemolyticus*, and *Vibrio vulnificus*), *Staphylococcus* spp (e.g., *Staphylococcus aureus*), *Yersinia* spp. (e.g, *Yersinia enterocolitica*), and the like, and chemical agents including, but not limited to, pesticides, toxins including ricin, botulin, aflatoxins, pyrrolizidine alkaloids, scombrotoxins, neurotoxin, mycotoxins such as ochratoxin A toxins, patulin toxins, *fusarium* toxins (e.g., fumonisins, trichothecenes including deoxynivalenol and zearelenone), and marine toxins such as ciguatera toxin, shellfish toxin, and tetrodotoxin, cyanide, nicotine, dioxin, polychlorinated phenyls, furans, heavy metals such as arsenic, lead, and mercury, histamine, histadine, and the like. The reagents can further be selected from those that can detect allergens such as those found in almonds, eggs, gliadin, milk, peanut, soy residues, and the like.

In a further embodiment of the present invention, suitable reagents can be selected from those that can provide detection for harmful contaminants such as radioactive agents including, but not limited to, radioactive isotopes of uranium, cesium, xenon, iodine, potassium, strontium, plutonium, iridium, and thorium.

Figure 2:
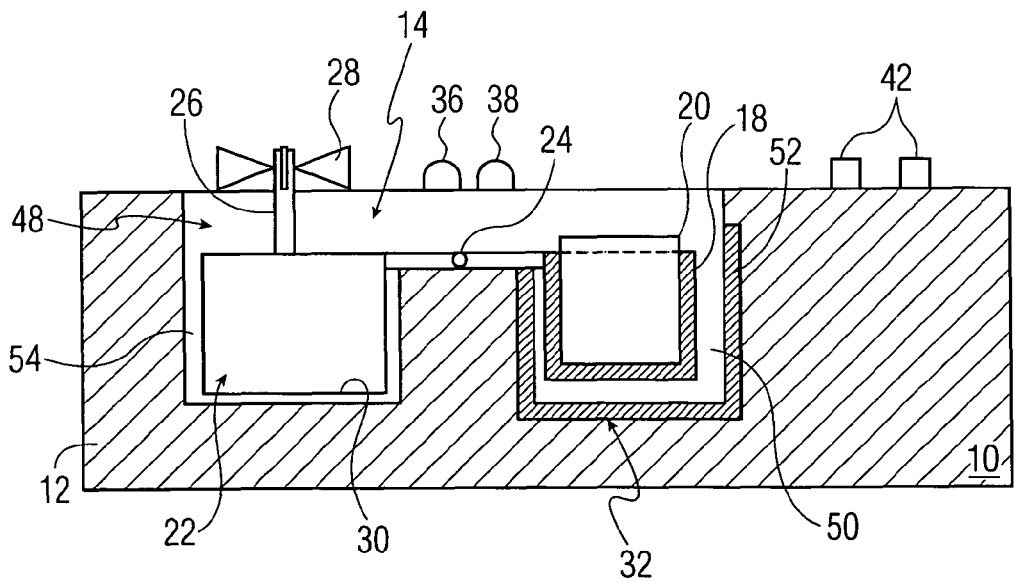
FIG. 2 is a partial cross-sectional view taken along lines 2-2 of FIG. 1 in accordance with the present invention.

Referring to FIG. 2, the food testing device 10 includes a recessed area 48 for accommodating the liquefier assembly 14. As discussed previously, the disposable container 20 holding the food sample, is retained in the vessel 18 of the liquefier assembly 14. The vessel 18 is located in a sample well 50 of the recessed area 48. The radiation detector assembly 32 includes an ionizing radiation sensor 52 extending along the sample well 50 around the vessel 18. The blade housing 30 of the blade assembly 22 is movable about the hinge 24 between open and closed positions. In the open position, the blade housing 30 occupies a holding well 54 of the recessed area 48. In the closed position, the blade housing 30 couples with the vessel 18 and encloses the disposable container 20. The mixing blades 28 draw into contact with the food sample held within the container 20.

Once the housing 30 is securely coupled to the vessel 18, the blade assembly 22 is activated through the power switch 16. The mixing blades 28 are driven for a sufficient time to breakup the food sample and convert it into a soft paste or thick liquid form. During the blending of the food sample, the radiation detector assembly 32 can be used to measure the ionizing radiation in the food sample. The indicator assembly 34 (see FIG. 1) determines whether the measured ionizing radiation exceeds normal background radiation levels, and alerts accordingly. Thereafter, the blade housing 30 is moved to an open position, and the mixing blades 28 are withdrawn from the container 20. A test assay can be implemented to analyze the food sample from the container as will be described hereinafter.

Figure 3:
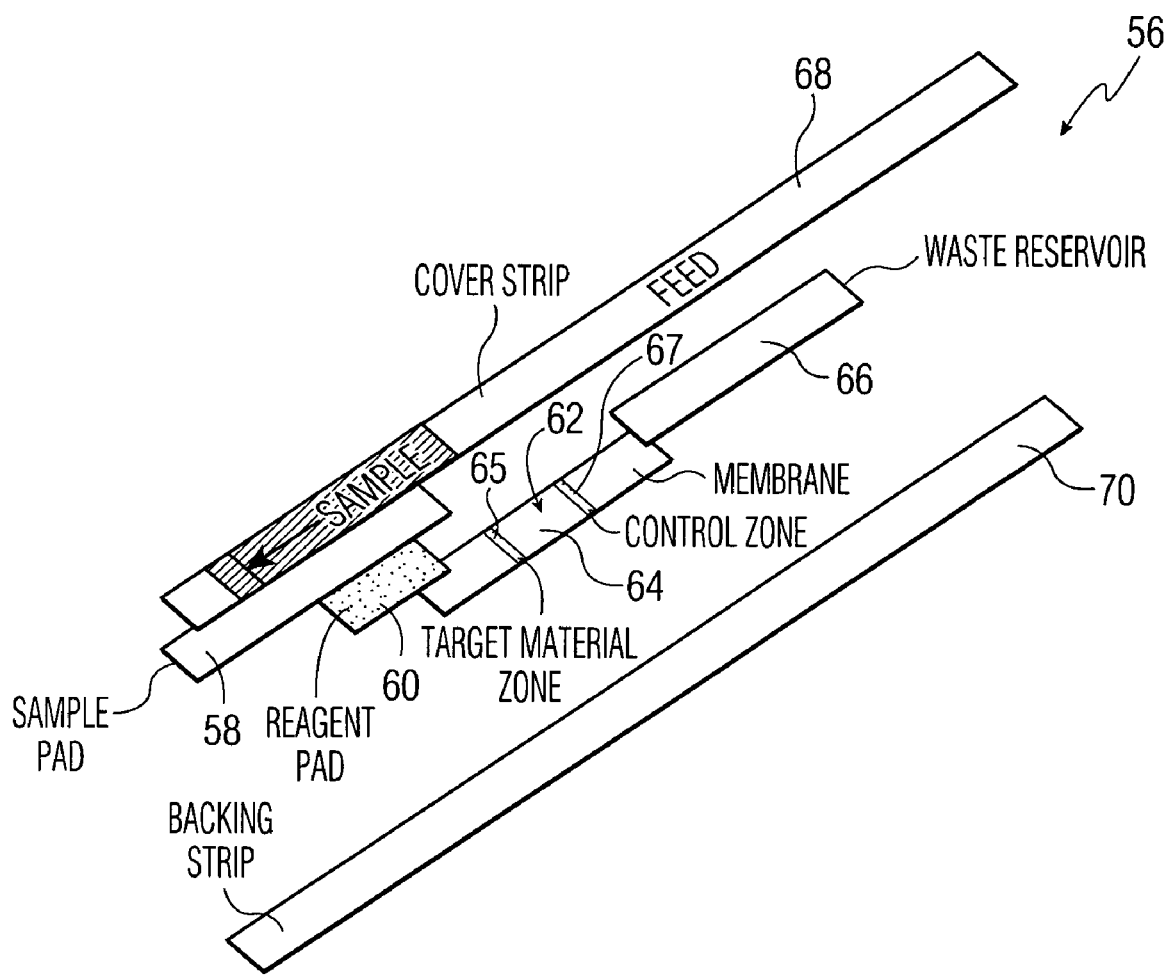
FIG. 3 is an exploded assembly view of a lateral flow assay for one embodiment of the present invention.

Referring to FIG. 3, a test assay is shown in the form of a lateral flow assay 56 for a preferred embodiment of the present invention. The lateral flow assay 56 is illustrated as an exploded assembly view. The lateral flow assay 56 can be fabricated to test for a single analyte or multiple analytes. The results of the assay 56 can be visually detected or machine-readable using suitable optical readers or scanners in combination with appropriate software programs. While the lateral flow assay 56 shown in FIG. 3 represents only one embodiment, it will be understood that the present invention is not limited as such.

As shown in FIG. 3, the lateral flow assay includes a sample pad 58 in contact with a reagent pad 60. The reagent pad 60 is in fluid communication with a membrane 62 comprising a test zone 64. The membrane 62 is in fluid communication with a waste reservoir 66. The sample pad 58, the reagent pad 60, the membrane 62 and the waste reservoir 66 are inserted and sandwiched between a cover strip 68 and a backing strip 70.

The sample pad 58 is disposed at the sample input end of the lateral flow assay 56. The sample pad 58 is dipped into the food sample, a portion of which is drawn through capillary action into the sample pad 58. The sample is then wicked from the sample pad 58 through the reagent pad 60, which contains reagents (e.g., antibodies) specific for a target substance or analyte representing the harmful food contaminant, conjugated to labeled or colored particles. If the target substance or contaminant is present, the target substance or contaminant binds to the particle conjugated reagent. The target substance-reagent-particle complex then leaves the reagent zone and travels through the membrane 62 into the test zone 64 thereof. The test zone 64 contains fixed anti-target substance reagents that captures the complex, and produce a visible cue such as a colored line 65. The remainder of the sample continues to migrate to the end of the membrane 62 where it is deposited into the waste reservoir 66.

The reagent pad 60 can further include a control immune complex that is eluted by the sample regardless of the presence of the target substance. The control conjugate migrates through the membrane 62 to the control zone where it forms a second visible cue such as a colored line 67. Regardless of the presence or absence of the target substance, the control line forms in the control zone to ensure the test assay is working properly. Note that a plurality of assays such as lateral flow assays 56 in the form of dipsticks can be held in the storage area 42, each for testing for a single contaminant. However, it is preferred that each test assay be capable of testing for a plurality of contaminants to the greatest extent possible.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A method for providing a device for testing for the presence of harmful contaminants in a food sample, comprising:

forming in a substrate a vessel comprising an open top and an interior cavity in communication with the open top, wherein said interior cavity is adapted for receiving and accommodating a disposable container to hold a food sample;

hingedly connecting a mechanical liquefier to the open top of said vessel, said mechanical liquefier being movable to a closed position for sealing the open top of the vessel;

configuring said mechanical liquefier with a blade assembly insertable into a disposable container in said interior cavity of said vessel in the closed position for mechanically converting the food sample into a liquefied form;

installing a radiation detector into said substrate proximate said vessel for indicating the presence of ionizing radiation in the food sample at amounts exceeding normal background levels to detect the presence of a radioactive agent as the harmful contaminant; and forming in said substrate a test assay supply compartment for containing at least one test assay, the test assay comprising at least one assay reagent having an affinity for at least one harmful contaminant.

2. A method for providing a device for testing for the presence of harmful contaminants in a food sample, comprising:

forming in a substrate a vessel comprising an interior receiving area having an open top, wherein said interior receiving area is adapted for receiving a disposable sample container to hold a food sample;

hingedly connecting a mechanical liquefier to the open top of said vessel, said mechanical liquefier being movable to a closed position for sealing the open top of the vessel;

configuring said mechanical liquefier with a blade assembly insertable into a sample container held in said interior receiving area of said vessel in the closed position for mechanically converting the food sample into a liquefied form;

installing a radiation detector into said substrate proximate said vessel for indicating the presence of ionizing radiation in the food sample at amounts exceeding normal background levels to detect the presence of a radioactive agent as a harmful contaminant;

installing into said substrate a display device operatively associated with the radiation detector for informing a user of the presence of a radioactive agent;

forming in said substrate a test assay supply compartment for containing at least one test assay, the test assay comprising at least one assay reagent having an affinity for at least one harmful contaminant; and installing in said substrate a timer for tracking and measuring the time necessary to complete the detection process of the corresponding assay.

* * * * *